(12) United States Patent
Sundstrom et al.

(10) Patent No.: US 9,234,229 B2
(45) Date of Patent: Jan. 12, 2016

(54) HIGH THROUGHPUT SYSTEM FOR ISOLATION, GROWTH, AND DETECTION OF LIPID INCLUSIONS IN BACTERIA

(75) Inventors: Eric R. Sundstrom, Menlo Park, CA (US); Craig S. Criddle, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 746 days.

(21) Appl. No.: 12/928,312

(22) Filed: Dec. 7, 2010

(65) Prior Publication Data
US 2011/0160067 A1    Jun. 30, 2011

Related U.S. Application Data

(60) Provisional application No. 61/283,811, filed on Dec. 8, 2009.

(51) Int. Cl.
*C12Q 1/04* (2006.01)
(52) U.S. Cl.
CPC ........................................ *C12Q 1/04* (2013.01)
(58) Field of Classification Search
None
See application file for complete search history.

(56) References Cited

U.S. PATENT DOCUMENTS

| | | | |
|---|---|---|---|
| 5,151,347 A * | 9/1992 | Delente et al. | 435/3 |
| 6,982,161 B1 | 1/2006 | Herrema et al. | |
| 7,579,176 B2 | 8/2009 | Herrema et al. | |
| 2007/0072194 A1* | 3/2007 | Alper et al. | 435/6 |
| 2010/0190221 A1 | 7/2010 | Herrema et al. | |
| 2010/0255540 A2 | 10/2010 | Herrema et al. | |

FOREIGN PATENT DOCUMENTS

WO    WO/2007/024255    3/2007

OTHER PUBLICATIONS

Greenspan et al (1985 J. Cell Biol 100:965-73).*
Verlinden et al. Bacterial synthesis of biodegradable polyhydroxyalkanoates. Journal of Applied Microbiology ISSN 1364-5072, 2007.
Dias et al. Recent Advances in Polyhydroxyalkanoate Production by Mixed Aerobic Cultures: From the Substrate to the Final Product. Macromol. Biosci. 2006, 6, 885-906.

* cited by examiner

*Primary Examiner* — Christopher M Gross
(74) *Attorney, Agent, or Firm* — Lumen Patent Firm

(57) ABSTRACT

A method of high throughput growth and quantitative analysis of microorganisms is provided that includes providing a microtiter plate growth and gas delivery system having well plates disposed for growth of the microorganisms, and providing a spectroscopic screening system disposed to analyze lipid inclusions of the microorganisms.

19 Claims, 3 Drawing Sheets

HIGH THROUGHPUT SYSTEM FOR ISOLATION, GROWTH, AND DETECTION OF LIPID INCLUSIONS IN BACTERIA

CROSS-REFERENCE TO RELATED APPLICATIONS

This application claims priority from U.S. Provisional Patent Application 61/283,811 filed Dec. 8, 2009, which is incorporated herein by reference.

FIELD OF THE INVENTION

The present invention relates to methods and systems for parallel growth and analysis of many replicate fermentations.

BACKGROUND OF THE INVENTION

Current approaches towards commercial production of PHB fall generally into two categories: nonsterile approaches in which PHB production is induced through environmental conditions, or genetic engineering approaches in which single strains are engineered for high production and rapid growth. In the first case, a vast number of conditions must be analyzed to determine which conditions select for promising microbes, and which conditions induce high PHB production. In the second case, libraries of mutant strains must be analyzed for high performing cells.

What is needed is a high throughput system that reduces the time required per replicate. What is further needed is a method and system directed to accelerating the development of high yield strains and conditions.

SUMMARY OF THE INVENTION

To address the needs in the art, a method of high throughput growth and quantitative analysis of microorganisms is provided that includes providing a microtiter plate growth and gas delivery system having well plates disposed for growth of the microorganisms, and providing a spectroscopic screening system disposed to analyze lipid inclusions of the microorganisms.

According to one aspect of the invention, the spectroscopic screening system includes a fluorescent screening system. In one aspect the fluorescent screening includes lipophilic fluorescent stains. Further, the lipophilic fluorescent stain can include Nile Red. In another aspect the fluorescent screening includes a flow cytometry screening system. Additionally, the fluorescent screening can include a plate reader screening system.

In another aspect of the invention, the microorganisms can include bacteria, eukaryota, or archaea, where the bacteria can be methanotrophic.

In yet another aspect of the invention, the microorganisms are grown in a pure culture.

In a further aspect of the invention, the microorganisms are grown in a mixed culture. Here, the mixed culture can contain at least two known pure cultures.

According to one aspect of the invention, the microorganisms are grown in an enrichment culture, where the enrichment culture can contain an unknown consortium of microorganisms. In one aspect, the source of the microorganisms can include soil, activated sludge, or other natural environments.

According to a further aspect of the invention, a controlled gas mixture is delivered to the plates. In one aspect, the gas mixture can include methane, nitrogen, oxygen, carbon dioxide, carbon monoxide, hydrogen, ethane, propane, or other gaseous hydrocarbons.

In yet another aspect of the invention, the lipid inclusions can include long-chain fatty acids.

According to one aspect of the invention, the lipid inclusions can include biological polyesters. Here, the biological polyesters can include polyhydroxyalkanoates (PHAs). Further, the PHAs can include polyhydroxybutyrate (PHB).

In another aspect of the invention, the optical system can be Raman spectroscopy.

In a further aspect of the invention, gas flow across the microtiter plate growth and gas delivery system can be a continuous gas flow or a varied gas flow.

In one aspect of the invention, a gas flow across the microtiter plate growth and gas delivery system includes a concentration gradient of gas constituents along the microtiter plate.

In another aspect of the invention, the microtiter plate growth and gas delivery system can include a light source disposed to culture photosynthetic organisms.

DETAILED DESCRIPTION

Biologically produced poly-hydroxyalkanoates (PHAs) represent a biodegradable and renewable alternative to petroleum based plastics. A variety of species and consortia are under investigation for commercial PHA production, including methanotrophic bacteria known to produce poly-β-hydroxybutyrate (PHB) under conditions of unbalanced growth. Complete study of the factors affecting methanotrophic growth and PHA production is currently limited by the modest throughput of available culture and analysis methods.

Figure 1:
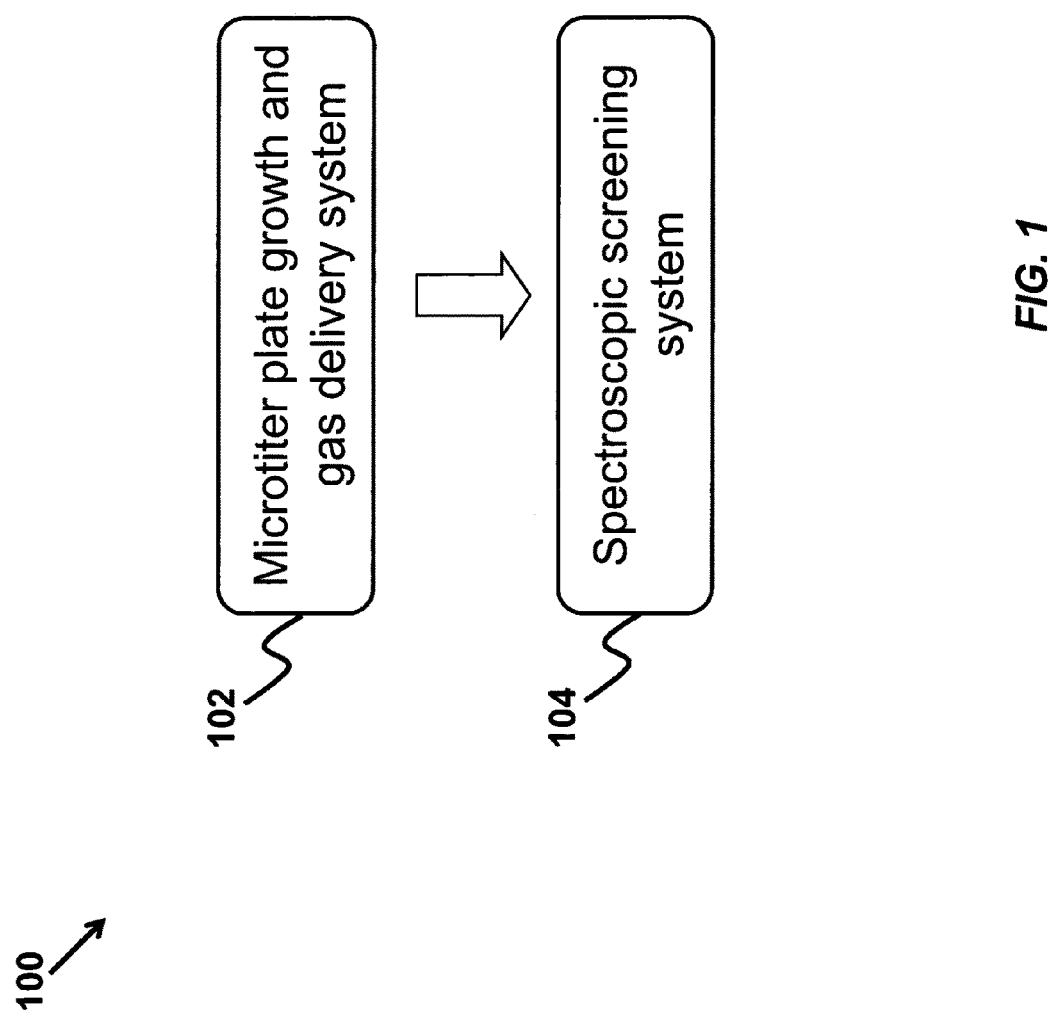
FIG. 1 shows a flow diagram of the steps high throughput growth and quantitative analysis of microorganisms, according to one embodiment of the invention.

FIG. 1 shows a flow diagram of the steps high throughput growth and quantitative analysis of microorganisms 100, according to one embodiment of the invention. The current invention includes providing a microtiter plate growth and gas delivery system 102 having well plates disposed for growth of the microorganisms, and providing a spectroscopic screening system 104 disposed to analyze lipid inclusions of the microorganisms. As compared to gas chromatographic methods, one embodiment of the invention provides flow cytometric analysis of cells stained with Nile Red dye to quantify PHA production using only a fraction of the biomass and handling time. Reduced biomass allows for growth in aerated microtiter plates, resulting in two order of magnitude savings in handling time per replicate. A high-throughput system is provided to optimize liquid media for increased PHB production.

In one embodiment of the invention, the microorganisms can include bacteria, eukaryota, or archaea, where the bacteria can be methanotrophic. Further, the microorganisms are grown in a pure culture, or grown in a mixed culture. Here, the mixed culture can contain at least two known pure cultures. In another embodiment, the microorganisms are grown in an enrichment culture, where the enrichment culture can contain an unknown consortium of microorganisms. According to the invention, the source of the microorganisms can include soil, activated sludge, or other natural environments.

The current invention combines two technologies: miniaturized growth with high agitation in microtiter plates, and quantitative Nile Red flow cytometric screening for polymer production. Combining flow cytometry with miniaturized growth allows for miniaturization and parallel manipulation throughout the entire cycle of isolation, growth, and analysis.

The current invention provides use of the microplate system for growth of methanotrophs. Further, the invention provides a procedure for staining and analyzing cells for PHB content without the need for individual manipulation, where the cell analysis can be a spectroscopic screening system. According to one aspect of the invention, the spectroscopic screening system is a fluorescent screening system that can include lipophilic fluorescent stains, and the lipophilic fluorescent stain can include Nile Red. In another aspect the fluorescent screening can include a flow cytometry screening system or a plate reader screening system.

In one aspect, the present invention provides a system for parallel growth and analysis of lipid producing bacteria. Commercially valuable lipid inclusions can be polymers such as poly(3-hydroxy)butyrate, as well as long chain fatty acids used for fuel production. According to one aspect of the invention, the lipid inclusions can also be biological polyesters, such as polyhydroxyalkanoates (PHAs).

An exemplary description recites detection of PHB for this invention, where PHB is a biologically produced polyester that is produced by a variety of bacteria under conditions of nutrient deprivation. When extracted, PHB has properties similar to those of polypropylene. Because PHB can be produced from a wide variety of inexpensive substrates, it represents a potentially inexpensive and biodegradable alternative to biologically produced plastics.

Maximizing growth rates and PHB content of cells is crucial to minimizing reactor size, substrate cost, and extraction cost. Currently, individual strains and conditions must be grown and analyzed individually, limiting the number of replicates per experiment. The current invention allows for parallel growth and analysis of hundreds of replicate fermentations. Increasing the rate of analysis dramatically decreases the time to market for new PHB technologies.

In addition to the process described above, further exemplary applications for the high-throughput microbioreactor system according to the current invention include use for non-PHB lipid inclusions such as other polyhydroxyalkanoates (PHAs), additional lipid polymers, and intracellular lipid fuel compounds (including biodiesel), and in addition to methanotrophs, the process allows screening of lipid compounds in non-methanotrophic bacteria, the invention allows for growth either under atmospheric conditions (without the gastight box), or under any customized atmosphere.

Figure 2:
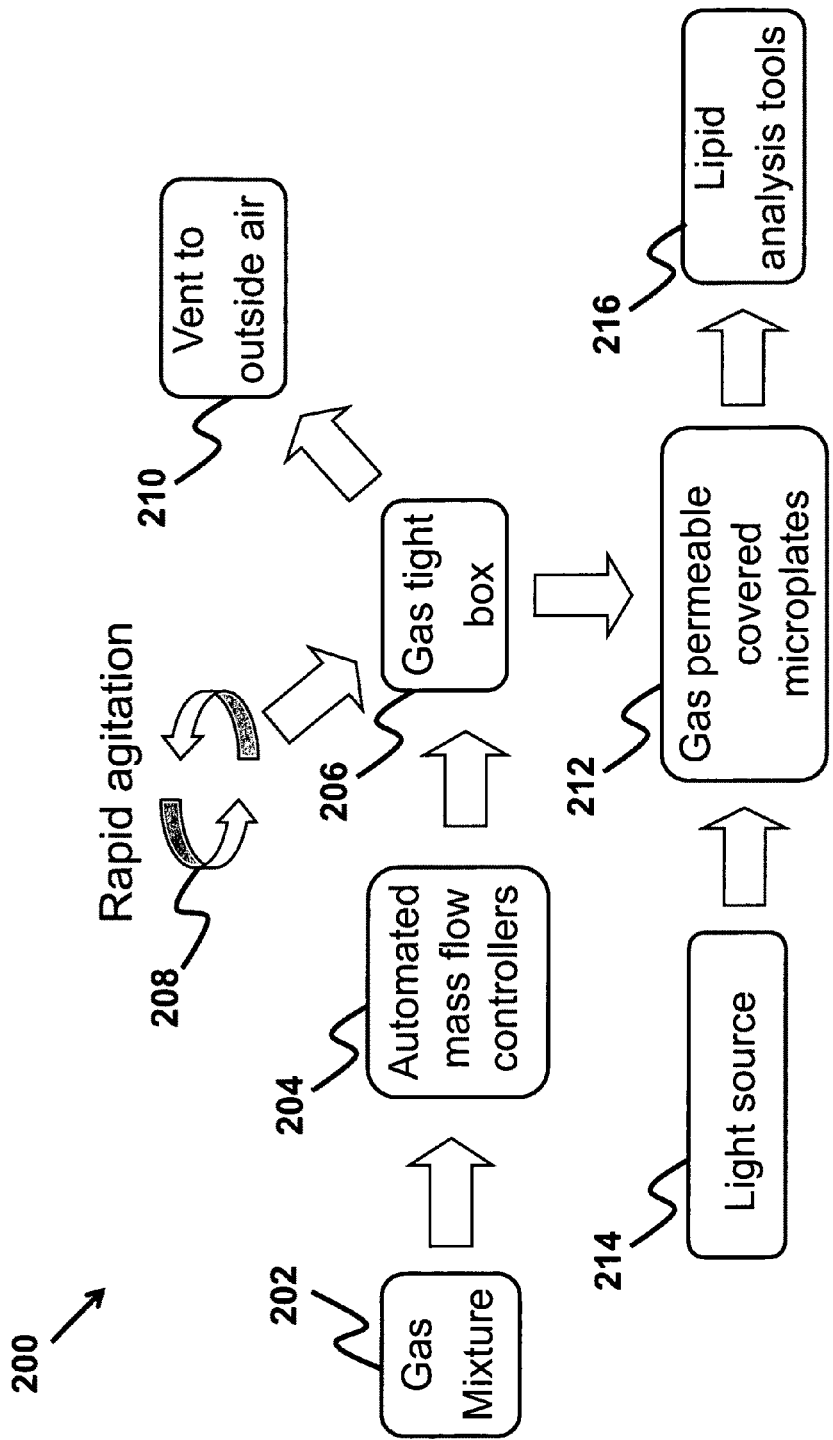
FIG. 2 shows a flow diagram of the steps of continuous gas flow and lipid analysis, according to one embodiment of the invention.

FIG. 2 shows a flow diagram of the steps of continuous gas flow and lipid analysis 200, according to one embodiment of the invention. As shown, a gas mixture 202 is provided to automated mass controllers 204. The automated mass controllers 204 regulate gas flow rates and constituent levels to a gas tight box 206, where the gas tight box 206 is subject to rapid agitation 208, where the gas tight box 206 further provides a vent 210 to outside air and a output port to the gas permeable covered microplates 212. In one embodiment of the invention, control over gas composition is improved through use of the flow-through gas system 200. This embodiment enables maintaining constant gas concentrations, even at very low levels, regardless of metabolic activity, and automated variation of gas composition over time. In another embodiment a light source 214 is provided, where the system is capable of culturing photosynthetic organisms. In further embodiment, alternative lipid analysis tools 216 are provided that include use of fluorescent plate readers, use of alternative lipid-specific fluorescent dyes, and using Raman spectroscopy, which also allows differentiation between lipid compounds.

Figure 3A:
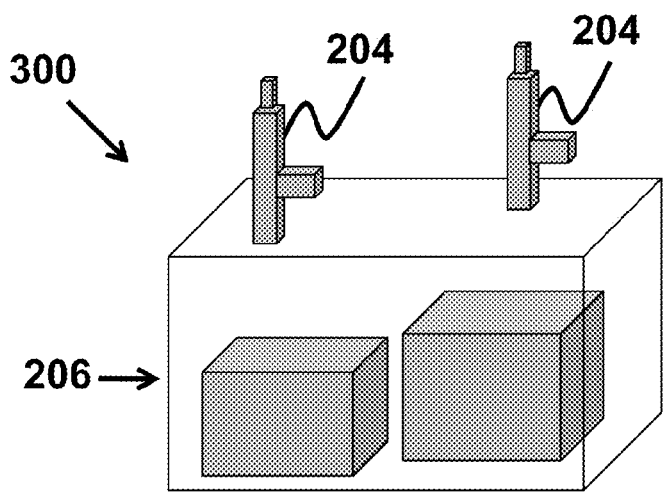
FIG. 3a-3c show an exemplary apparatus microtiter plate growth system, according to one embodiment of the invention.
Figure 3B:
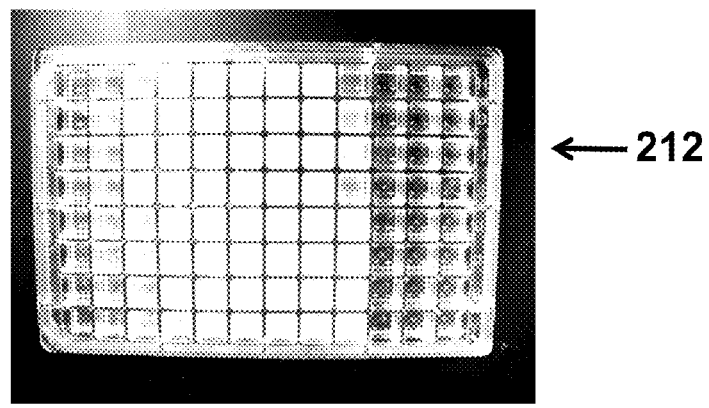
Figure 3C:
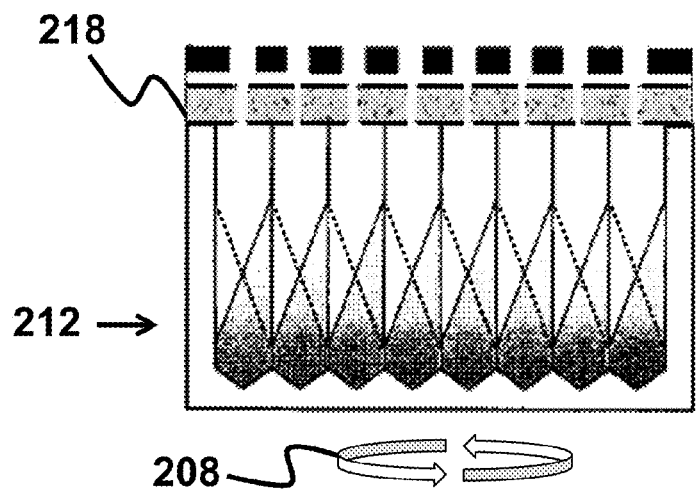

FIG. 3a-3c show elements of one embodiment of the high throughput microplate growth system 300, where FIG. 3a shows the gas tight box 206 having automated gas flow controllers 204 with microplates 212 contained in the gas tight box 206. This allows for consistent, highly agitated growth, for example in 96 well microplates 212, as shown FIG. 3b, which is top view of the 96 well microplates 212, without risk of cross-contamination or excessive evaporation. FIG. 3c shows a side view of the microplates 212 covered by gas permeable membranes 218, clamped to shaker tables under high agitation 208. Gas permeable plate covers allow gas transfer while preventing evaporation and cross-contamination. High agitation creates complete mixing within each well. For example, with production of methanotrophic organisms, the plates 212 are placed inside the gas tight box 206 filled with a 50:50 methane oxygen mixture. For targeting aerobic heterotrophs, the system is provided either open to the atmosphere or incubated with 100% oxygen. Each well can be inoculated with an individual strain, grown in individual media. Growth is then quantified by periodically removing the plates and measuring optical density on a plate reader 216. Repeated scanning of optical density allows measurement of growth rates. PHB content is determined by automated flow cytometry after staining with Nile red.

According to one embodiment of the invention, a controlled gas mixture is delivered to the plates. In one aspect, the gas mixture can include methane, nitrogen, oxygen, carbon dioxide, carbon monoxide, hydrogen, ethane, propane, or other gaseous hydrocarbons.

In one aspect of the invention, lipid production is quantified by measuring Nile Red fluorescence on a flow cytometer. Plates can be stained in bulk using multi-channel pipettes for reagent addition and a microplate centrifuge is used for washing and pelleting of cells. The plates can then be read on a flow cytometer equipped with a microplate autosampler. Nile Red dye is fluorescent only within the hydrophobic phase, and therefore cells with higher PHB content fluoresce more intensely. This effect can be quantitatively linked to actual PHB content of the cell.

The growth system according to the invention is highly compatible with existing high-throughput systems, as most rely on 96 well plates. In addition, cell sorters are capable of isolating individual cells into microplates. Coupling with a cell sorter allows targeted isolation and characterization of cells, all within a single integrated system.

Large-scale microplate screening has uses across the spectrum of research on PHB production. For example, the current invention is useful for screening large libraries of cells for viability, growth rate, and polymer production under varying conditions. In a further example, the invention is useful for screening single isolates or communities for polymer production across an enormous range of conditions (media optimization). In one aspect, the invention is useful for isolating and characterizing high performance mutants using cell sorting technology. Additionally, the invention enables analyzing the growth conditions selective for PHB producing organisms by exposing a single diverse inoculum to a range of conditions. The invention enables high throughput analysis of reactor samples, or isolation of methanotrophs without use of agar.

The current invention enables a multiple order of magnitude increase in screening efficiency, vastly increasing the number of isolates and conditions that can be screened quantitatively for polymer production. The current invention alleviates the need for each of the replicate fermentations to be prepared and analyzed individually. Thus, the invention further increases efficiencies through the use of multiple well robotic techniques found in biotechnology.

In another aspect, the invention enables high throughput growth and quantitative analysis of lipid content in bacteria, resulting in at least order of magnitude reductions in handling time per replicate while producing reliable data on biomass, growth rates, and lipid content. Because the invention enables growth in well plates, enormous advantages over traditional isolation on plates, or fermentation in shake flasks are provided. By coupling with flow cytometry or other analysis tools instead of the more conventional gas chromatographic method, the invention enables smaller cell volumes to be analyzed, eliminating the need for larger fermentations. Unlike isolation on agar plates, the current invention allows growth conditions in well plates to mimic those of commercial production. Because number of organisms cannot be isolated on solid plates, preferring liquid culture, as is the case with many methanotrophs, the cultivation system of the current invention therefore increases the suitability of methanotrophic organisms for biotechnology applications.

According to another aspect of the invention, a fluorescent plate reader is substituted for automated flow cytometry, thus increasing the throughput. In another aspect, quantitative Nile Red screening can also been used as a measure of lipid content for the production of biodiesel. Further, the invention could also be used for biodiesel fermentations, or any other application requiring high aeration for growth and accurate quantification of lipid production. A variety of other lipophilic dyes could be substituted for Nile Red, to provide similar results.

Some exemplary applications of the invention include providing high throughput screening of cultures and enrichments for high bioplastic or biodiesel production, providing media optimization for high yields and high growth rates, and enabling isolation of high performance strains.

In one embodiment of the invention, gas flow across the microtiter plate growth and gas delivery system can be a continuous gas flow or a varied gas flow, and can further include a concentration gradient of gas constituents along the microtiter plate.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the invention can include provisions for the imposition of temperature gradients across the plates, such as by continuous addition of pre-warmed gases at one end of the gas tight box with continuous introduction of cooling fluids at the other points. Another variation of the invention can include provisions for multiple entry and exit points for gases so as to enable spatial variability in the flow of gases through the box. A further variation can include provisions for gas sampling ports to enable periodic extraction of gas samples for assay of gas phase concentrations. Additionally, provisions can be included for wavelength variations in the added light source used for cultivation of photosynthetic microorganisms. Finally, the invention can include provisions for temporal and spatial variations in the light source used for cultivation of photosynthetic microorganisms.

All such variations are considered to be within the scope and spirit of the present invention as defined by the following claims and their legal equivalents.

What is claimed:

1. A method of providing a high throughput growth and quantitative analysis of microorganisms, comprising:
   a. screening a throughput of cultures for bioplastic enrichment from an array of lipid producing bacteria using a microtiter plate growth and gas delivery system, wherein said microtiter plate growth and gas delivery system comprises well plates disposed for growth of microorganisms and a spectroscopic screening system disposed for analyzing said bioplastic and a gas delivery system comprising controlled gas flow of methane, nitrogen, oxygen, carbon dioxide, carbon monoxide, hydrogen, ethane, propane, or other gaseous hydrocarbons as a continuous gradient along the microtiter plate;
   b. isolating lipid producing bacteria of said bioplastic;
   c. inducing production of bioplastic;
   d. determining a growth condition for enriching bioplastic production using said spectroscopic screening of said microtiter plate growth and gas delivery system.

2. The method according to claim 1, wherein said spectroscopic screening system comprises a fluorescent screening system.

3. The method according to claim 2, wherein said fluorescent screening comprises lipophilic fluorescent stains.

4. The method according to claim 3, wherein said lipophilic fluorescent stain comprises Nile Red.

5. The method according to claim 2, wherein said fluorescent screening comprises a flow cytometry screening system.

6. The method according to claim 2, wherein said fluorescent screening comprises a plate reader screening system.

7. The method according to claim 1, wherein said microorganisms are selected from the group consisting of bacteria, eukaryota, and archaea.

8. The method according to claim 7, wherein said bacteria comprises methanotrophic.

9. The method according to claim 1, wherein said microorganisms are grown in a pure culture.

10. The method according to claim 1, wherein said microorganisms are grown in a mixed culture.

11. The method according to claim 10, wherein mixed culture contains at least two known pure cultures.

12. The method according to claim 1, wherein said microorganisms are grown in an enrichment culture.

13. The method according to claim 12, wherein said enrichment culture contains an unknown consortium of microorganisms.

14. The method according to claim 13, wherein the source of said microorganisms selected from the group consisting of soil, activated sludge, and other natural environments.

15. The method according to claim 1, wherein said concentration gas gradient of gas constituents comprises a controlled gas mixture that is delivered to said plates.

16. The method according to claim 1, wherein said lipid inclusions comprise biological polyesters.

17. The method according to claim 16, wherein said biological polyesters comprise polyhydroxyalkanoates (PHAs).

18. The method according to claim 17, wherein said PHAs comprise polyhydroxybutyrate (PHB).

19. The method according to claim 1, wherein said microtiter plate growth and gas delivery system comprises a light source disposed to culture photosynthetic organisms.

\* \* \* \* \*